United States Patent [19]

Hennart

[11] 4,015,970
[45] Apr. 5, 1977

[54] GRANULAR PRODUCTS FOR SOIL TREATMENT

[75] Inventor: Claude Hennart, Aubervilliers, France

[73] Assignee: Airwick Industries, Inc., Carlstadt, N.J.

[22] Filed: Oct. 3, 1974

[21] Appl. No.: 511,726

Related U.S. Application Data

[63] Continuation of Ser. No. 198,550, Nov. 15, 1971, abandoned, which is a continuation-in-part of Ser. No. 854,403, Sept. 2, 1969, abandoned.

[30] Foreign Application Priority Data

Sept. 6, 1968 France .......................... 68.165314
Aug. 20, 1970 France .......................... 70.30538
Apr. 8, 1971 France .......................... 71.12474

[52] U.S. Cl. .................................... 71/11; 71/27; 71/34; 71/53; 71/63; 71/64 E; 71/DIG. 2
[51] Int. Cl.$^2$ .................................... C05G 3/00
[58] Field of Search ............. 71/53, 63, 64 E, 64 F, 71/1, 11, 27, 31, 34, DIG. 2

[56] References Cited

UNITED STATES PATENTS

| 3,150,160 | 9/1964 | Dexter | 71/DIG. 2 |
| 3,325,276 | 6/1967 | Feller | 71/64 E |
| 3,533,776 | 10/1970 | Coates | 71/53 X |
| 3,560,192 | 2/1971 | DiCicco | 71/53 X |
| 3,660,070 | 5/1972 | Maruta et al. | 71/64 E |
| 3,799,756 | 3/1974 | Keller | 71/DIG. 2 |

FOREIGN PATENTS OR APPLICATIONS

| 42,564 | 1971 | Japan |
| 13,083 | 1972 | Japan |

Primary Examiner—Frank A. Spear, Jr.
Assistant Examiner—Ferris H. Lander
Attorney, Agent, or Firm—Wenderoth, Lind & Ponack

[57] ABSTRACT

Granular products for the treatment of soil are described which comprises a central solid nucleus containing fertilizer, herbicide, or a mixture of fertilizer and herbicide, all soluble in water without decomposition, as well as, about each product a coating consisting of solid materials at least 40% of which are soluble in water without decomposition, and at least 15% of which consist of active material different from that of the nucleus, and a polymeric resin the amount of which does not exceed 10% of the total weight of the coating. Comparative tests are described which show that these novel granular products can be as readily dissolved in the soil as uncoated fertilizer granules.

19 Claims, 3 Drawing Figures

GRANULAR PRODUCTS FOR SOIL TREATMENT

This application is a continuation of application Ser. No. 198,550, filed Nov. 15, 1971, and now abandoned which in turn is a continuation-in-part of my pending application Ser. No. 854,403 filed on Sept. 2, 1969 now abandoned.

The present invention relates to granular products for soil treatment, relating more particularly to the fertilization thereof and/or the destruction of pests and/or undesirable plant growth found therein or thereon.

The invention also concerns the manufacture of the granular material in question.

It is current practice to use fertilizer materials and antiparasitic, e.g. pesticidal or herbicidal, agents in granular form. This allows convenient distribution, either by hand or by any mechanical means.

An important problem exists when it is desired to combine products such as fertilizer and/or water-soluble herbicides with insecticides, fungicides, nematocides, and compounds capable of giving plants their necessary oligo-elements such as copper, magnesium, zinc, calcium, boron, molybdenum, magnanese, iron and nickel, or with herbicides or fertilizer less soluble or insoluble in water; this problem is particularly delicate when it is desired to give the combination a granular form. It is not generally possible to prepare satisfactory granules of such products by present granulation methods. One of the reasons for this resides in the fact that water-soluble fertiliser materials, for example, are in general produced and put on the market in the form of granules of dimensions between 1 and 7 mm. It is the same for certain water-soluble herbicides, such as, for example, sodium chlorate.

The production of homogeneous granular products containing both such fertilisers or herbicides and the active materials mentioned above thus necessitates a first operational stage consisting of reducing the different constituents to a fine powder by milling, then to re-unite them by means of a process involving, for example, a high pressure or a raised temperature. It is difficult to obtain sufficiently coherent granules at a reasonable industrial production rate without resorting to such a process. Now, it is well-known that the above noted additives generally resist such treatments badly. Besides, it can be dangerous to submit certain of the compounds noted to milling; this is the case, for example, with sodium chlorate. It is quite clear, also, that the destruction of the granular products by milling and the subsequent reproduction of a new granular product, involves an undesirable extra expense.

On the other hand, it is known to coat granules of water-soluble active substance, particularly fertilizers, by materials which retard their dissolution and thus their effect on plants, as, for example, liquid hydrocarbon or molten hydrocarbon normally solid at a temperature of below 50° C, or thermoplastic resin or plastics materials such as polyvinyl compounds, polyethylene, polypropylene, petroleum resin derivatives or analogous products insoluble in water such as bitumen, waxes or paraffin; such hydrophobic coats slow down considerably the diffusion of the products in water and, as a result, in the soil.

It is also known to augment the retarding effect of such coats by the incorporation therein of quantities of water-insoluble mineral materials, such as calcium carbonate, chalk, finely divided limestone rock, calcinated lime, gypsum, pure clays, powdered phosphate rock which has not been treated with acid to convert its phosphorus containing components into a form in which plants can absorb them, etc. Inert and water-insoluble organic substances have also been incorporated into the coatings.

Further, there have been described, products having a nucleus consisting of a fertilizer and a coating comprising a water-insoluble insecticide or herbicide and a binder comprising one or more hydrophilic materials such as emulsifiers. The object of such a combination is to obtain a suspension in water of the insoluble insecticide or herbicide at the moment of diffusion of the fertilizer.

As binder there has also been used polyethylene glycols of molecular weight between 2000 and 6000. However, the granular products thus obtained have the defect of being sticky and hygroscopic, so that the product forms lumps in the mass of granular product when the relative humidity reaches 70%.

It has been attempted to replace the polyethylene glycol by a polyoxyethylene derivative of higher molecular weight, but this substitution leads to industrial complications following from the increase in viscosity of the binder which must then either be used in molten state or in aqueous solution. In the first case the use of a heating material, in the second the necessity of drying an aqueous product considerably increase the cost price.

While all these known products, consisting of granules with coated nuclei, are made with the object of retarding the action of the active substances they contain, the object of the present invention is to prepare granular products composed of the substances mentioned above, the nuclei of which remain water-soluble, even when part of the additional active components is only slowly soluble in water and, as a result, in the soil.

Another object of the invention is to unite fertilizing and/or herbicidal active substances with one or more other materials mentioned above in the form of granules in which the constituents are not damaged by the operation.

Another object of the invention is to allow the combination of such active substances without the necessary use of heat or pressure and within a short time.

Another object of the invention is to combine fertilizing, insecticidal nematocidal, fungicidal substances furnishing oligo-elements to plants and/or herbicidal substances which are normally incompatible with one another and which cannot be mixed together.

Another object of the invention is the production of stable, coherent granular products in which the granules do not stick together throughout the period of storage during transport and during handling in the course of use.

All these objects and others which will become apparent in the description of the invention which follows are obtained by the granular products according to the invention, such as are defined hereafter.

The granular products for soil treatment according to the invention, comprise, per granule, (a) a central solid nucleus constituting at least about 65% by weight of the granule, this nucleus consisting, for at least 40% of its weight, of a material soluble in water without decomposition, consisting essentially of i. fertilizer or
    ii. herbicide or iii. a mixture of fertilizer and herbicide, with or without solid additive material selected from insecticides stable in average humidity, nematocides, fungicides and inert materials, (b) at least one coating covering the nucleus and constituting between about 1 and about 35% by weight of the granule, and consisting of one or several layers of
α particles of solid material
β solid polymeric resin, plasticised or non-plasticised, insoluble in water, present in quantity sufficient to bond the particles of solid material to one another and to the nucleus, and are characterised in that at least a portion of the said solid particles, constituting at least 40% by weight of the total weight of the coating, consists of material soluble in water without decomposition, in the ratio of at least 1 gram (g) of substance per 50 g water, that at least 15% by weight of the total weight of the particles of solid material is of active substance different from that of the nucleus and is selected from fertilizers, herbicides, insecticides stable in humid medium, nematocides, fungicides and substances furnishing oligo-elements to plants, that the average value of the major diameter of the said particles of solid material does not exceed 0.2 mm, and that the amount of the said polymeric resin does not exceed 10% of the total weight of the coating.

By "solubility in water" there is meant in this application a solubility of at least 1 g of substance per liter of water. Preferably the active substances in water without decomposition have a solubility of at least 1 g of per 100 g water.

By "fertiliser soluble in water without decomposition" is meant in this application a mineral or organic material capable of providing the soil with nitrogen, phosphorus and/or potassium in a form directly or indirectly assimilable by vegetation.

Such materials may contain nitrogen, preferably in the form of salts formed between nitric acid and alkali metal or alkaline earth metal or ammonium ions, or in the form of salts formed between ammonium ion and acids other than nitric acid which are agriculturally acceptable, or in the form of organic compounds like urea.

Such materials may contain phosphorus, preferably in the form of salts formed between phosphoric acids and alkali metal or alkaline earth metal or ammonium ions.

Such materials may contain potassium, preferably in the form of salts formed between the potassium ion and agriculturally acceptable acids.

According to a particularly preferred embodiment of the invention, the nucleus contains one or more of the following fertilizers: ammonium sulphate, ammonium chloride, ammonium nitrate, ammonium phosphates, sodium nitrate, potassium nitrate, calcium nitrate, potassium chloride, potassium sulphate, potassium carbonate, sodium phosphate, potassium phosphate, and urea.

According to another embodiment of the invention, the nucleus contains one or more herbicides, selected from derivatives of phenoxyacetic acid, phenoxypropionic acid, phenoxybutyric acid, 4-amino-3,5,6-trichloro-picolinic acid, sym. triazine, phenoxyethyl-sulphuric acid, halogenated benzoic acid, halogenated acetic acid, halogenated propionic acid, phenylurea, or bipyridylium, and certain mineral salts appearing in the following list of preferred herbicides: sodium chlorate, sodium or potassium 2,4-dichloro-phenoxyacetate, sodium or potassium 4-chloro-2-methyl-phenoxyacetate, sodium or potassium 2,4,5-trichloro-phenoxyacetate, sodium or potassium 2-(4-chloro-2-methylphenoxy)-propionate, sodium or potassium 2-(2,4-dichlorophenoxy)-propionate, sodium or potassium 2-(2,4-dichlorophenoxy)-propionate, sodium or potassium 4-(2,4-dichlorophenoxy)-butyrate, sodium or potassium 4-(4-chloro-2-methylphenoxy)-butyrate, sodium or potassium 4-(2,4,5-trichlorophenoxy)-butyrate, sodium or potassium 4-amino-3,5,6-trichloropicolinate, sodium 2-(2,4-dichlorophenoxy)-ethylsulphate, 2,3,6-trichlorobenzoic acid, 3,6-dichloro-2-methoxybenzoic acid, sodium chloracetate, trichloracetic acid, sodium 2,2-dichloropropionate, sodium 2,2,3-trichloropropionate, N,N-dimethyl-N'-phenyl urea and its trichloracetic salt, the trichloracetate of N,N-dimethyl-N'-(4-chlorophenyl) urea, copper sulphate, iron sulphate, 1,1'-dimethyl-4,4'-bipyridylium dichloride, 1,1'-bis-(3,5-dimethyl-4-morpholinyl)-carbonylmethyl-4,4'-bipyridylium dichloride, 9,10-dihydro-8a-10a-diazaphenanthrene dibromide, 3-amino-1,2,4-triazole, and sym. triazines falling under the formula

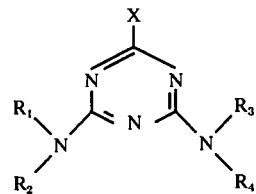

in which X is chlorine, methoxy or methylthio, $R_1$, $R_2$, $R_3$ and $R_4$ are the same or different and are each hydrogen or an alkyl residue containing 1–5 carbon atoms in branched or straight chain and optionally bearing a methoxy group.

Inert materials which can be incorporated in the nucleus are preferably dried clay, calcium carbonate, brick, pumice, pyrophyllite, sulphur, kaolin, dolomite, plaster, wood flour, sugars, sodium chloride or sodium sulphate.

The average value of the major diameter of the nuclei of granules in products according to the invention is preferably between 0.6 and 16 mm, more preferably between 1 and 8 mm. The total weight of the coating of the granules is preferably between 3 and about 35% and more preferably between 10 and 35% of the total weight of the granular product. The average value of the major diameter of the granules in the product of the invention is, for this reason, generally between about 0.6 and 22 mm, and preferably between 1.2 and 10 mm.

The presence of a powder comprising at least 40% by weight of water-soluble materials, active and/or inert, in the macromolecular resin used in an essential feature of the invention.

As a result of this high content of water-soluble particles in the coating and do to their statistical distribution throughout the latter, there is sufficient direct contact left between the particles to form a network of veins formed by contiguous solid waer soluble particles.

This network of veins is readily solubilised as soon as it comes into contact with the moisture of the soil, largely disintegrating the coating and/or opening up channels and pores through the same, through which water can reach the central nucleus without any "retarding effect".

The central nucleus is thus disintegrated and dissolved as quickly as if there were no coating at all, and the active materials are set free without any delay.

Preferably, the average value of the major diameter of the particles of the powder is between 0.001 and about 0.1 mm. Preferably, the water-soluble particles of the coating comprise at least one active material and optionally at least one inert material.

Preferably, the particles being part of the coating contain a proportion of active materials of about 15–85%.

The macromolecular resin serving as binder is advantageously a homopolymer, a copolymer or a mixture of these polymers, each of these types of polymer being optionally plasticised.

The quantity of such resin incorporated in the coat is preferably between 0.2 and 10% of the weight of the coat, more preferably 0.5 and 6depending on the nature of the resin, and most preferably between 1 and 3%.

This small proportion of resin permits binding the solid particles to one another and to the nucleus by constituting a discontinuous cement between the particles, but without interrupting contact between the particles completely, thus leaving the coating permeable to water.

The inert powders insoluble in the water used in the coating layer are preferably talc, kaolin, calcium carbonate, magnesia, mica, titanium oxide, zinc oxide, carbon black, sugar, starches or cereal flours.

The inert powders soluble in the water used in the coating layer are preferably alkali metal or alkaline earth metal salts compatible with the active materials of the product.

Preferably, the portion of the particles of solid material of the coat which consists of material soluble in water without decomposition, is between half and two thirds of the weight of the solid particles. In one of the variants of the granular products of the invention, the solid particles of the coating are all of active material. According to another variant the particles present in the coating which are of active material are all of water-soluble material; according to a third variant, 80% at most of the weight of active material is constituted by substances insoluble in water.

Among the active materials soluble in water which can be incorporated in the coating, there are, above all, the substances which provide plants with oligo-elements, such as the soluble salts or soluble complex compounds formed between agriculturally acceptable acids and magnesium, copper, zinc, calcium, manganese, iron and nickel ions, and the soluble salts formed between alkali metal or alkaline earth metal or ammonium ions and boric and molybdic acids.

The following macromolecular resins are suitable for use as binders in the coating:

polyethylenes, polypropylenes, polybutylenes and, more generally, polyolefins and copolymers thereof;

polyvinylesters such as polyvinyl acetate, propionate and butyrate;

polyvinyl halides such as polyvinyl chloride and polyvinylidene chloride;

copolymers of vinyl chloride and vinyl acetate;

copolymers of vinyl acetate and ethylene;

polyvinylethers such as polyvinyl butyl ethers;

polyvinyl acetals such as polyvinyl formal, polyvinyl acetal and polyvinyl butyral;

polystyrenes and polyvinyl toluenes;

cellulosic esters such as cellulose acetate, propionate, butyrate, phthalate and nitrate;

cellulose ethers such as the water-insoluble methyl ethers and ethylethers of cellulose, and the cellulose benzyl ethers;

polyisoprenes and polybutadienes;

polyacrylic esters such as poly(methyl acrylate) and poly(ethyl acrylate);

polymethacrylic esters such as poly(methyl methacrylate), poly(ethyl methacrylate) and poly(butyl methacrylate);

the so called "polyester" resins, made by the reaction of a polyacid with a polyol;

polyallylic esters such as poly(allyl-phthalate), -isophthalate), -maleate) and -cyanurate);

the so-called "polyamide" resins such as polycaprolactam, polyhexamethyleneadipamide and polyhexamethylenesebaceamide;

polyurethanes resulting from the condensation of a polyisocyanate with a polyol;

coumarone-indene resins.

The resin constituting the binder optionally contains one or more of the well-known plasticisers, and more in particular, the following: dimethyl, diethyl, dihexyl, dicyclohexyl, dioctyl and diphenyl phthalates, dibutyl, dioctyl and dibenzyl sebaceates, dibutyl, dioctyl, dinonyl and didecyl adipates, ethyl, isopropyl and butyl myristates, triacetin, and triphenyl, tricresyl, tri-(tert-butyl-phenyl), tri-(diphenyl)-, diphenylcresyl, phenyldicresyl, tributyl, trioctyl, tridecyl and tridodecyl phosphates.

When a plasticiser is used, this resin should contain between 5 and 40% of plasticiser, and preferably being between 10 and 30%, calculated on the weight of the resin.

The resin can optionally also contain a gloss-imparting agent, such as, for example, a natural or synthetic wax.

The resin can optionally also contain an ultra-violet light-absorbing agent, to protect the resin and/or the additional materials against the effects of such light, such agent being, for example, a benzotriazole derivative, a hydroxybenzophenone, an aryl salicylate, a substituted acrylonitrile or a hydroxyphenyltriazine.

The coating layer can optionally contain mineral, organic or metallic pigment particles.

The preferred organic pigments are those which have a very low or zero solubility in any solvent used and a high resistance to migration (exudation) in the particular resin used.

The granular products for soil treatment of the invention have the advantage of having a clean appearance and being dry and not dusty to the touch. Furthermore, they are not hygroscopic, which suppresses any risk of clumping in use.

Their coating layer is remarkably homogeneous, of substantially even thickness and very resistant to shocks and friction.

As indicated above, the granular product so made is easy to store and handle, since the granules do not stick to one another, even in a humid atmosphere.

In contrast, or contact with the humidity of the soil, the water-soluble particles encased in the resin rapidly diffuse into the soil and the active materials of the central nucleus dissolve in turn and pass through the layer which becomes immediately porous and permeable, practically without any retarding effect, i.e., for all practical purposes, about as quickly as if they were uncoated.

The manufacture of the granular product according to the invention starts from granular nuclei which are coated with macromolecular resin and onto which the particles of powder attach themselves.

The macromolecular resin is used as a solution in a volatile anhydrous organic solvent.

This solution advantageously contains 0.5 to 25% by weight of macromolecular resin, preferably 2–15%, calculated on the total weight of the solution.

Preferably, the solvents which vary depending upon the particular resin used, are chosen from those having a low boiling point. A non-limitative examples, there may be cited the following solvents corresponding to these desiderata: pentane, hexane, heptane and petroleum ethers, cyclohexane, benzene, toluene, propyl chloride, butyl chloride, methylenechloride, dichlorethane, dichloropropane, trichlorethane, trichlorethylene, chloroform, perchlorethylene, carbon tetrachloride, methanol, ethanol, propanol, isopropanol, butanol, 2-ethoxyethanol, ethyl oxide, isopropyl oxide, acetone, methylethylketone, methyl isobutyl ketone, cyclohexanone, isophorone, methyl acetate, ethyl acetate, isopropyl acetate, butyl acetate, methyl propionate, ethyl propionate, acrylonitrile, acetonitrile, and mixtures thereof.

The following table indicates, without being in any way limiting, some preferred correlations between various organic solvents and macromolecular resins.

Referring to the first embodiment of the invention shown in FIGS. 1 and 2, there is seen the granular product for the treatment of soil formed by a central nucleus 1 surrounded by a coating layer 2.

The shape of the central nucleus 1 is arbitrary; according to the mode of manufacture used, the nucleus may have for example, a regular, spherical or cylindrical shape, or, in contrast, an irregular shape, its greatest dimension advantageously remaining in the range of 0.6 to 16 mm. It may be obtained by any known means: granulation of active material in powder form bonded by compression and/or agglutination; granulation of active material, even liquids dispersed in an inert material bonded in the same manner as the preceding case, absorption or adsorption of the active material in an inert porous material, optionally followed by drying; mixture of the active material with an inert plastic material such as a clay, or artifically made plastic or fluid, the mixture being followed by drying or baking.

The coating layer 2 is, as is seen in FIG. 2, in the form of imprisioned particles which are particles 4 of active material, particles 5 of inert material and particles 6 of pigment bound together by a discontinuous cement of macromolecular resin. The particles of active material may be all of the same material or a mixture of different materials, and the same is true for the particles of inert material 5. As a portion amounting to at least 40% of the said particles is water-soluble, the soluble particles are forming a major portion of the coat which can thus also disintegrate rapidly in water.

To make the granular product according to the invention, a measured quantity of nuclei 1 is charged into

| | Polyvinyl chloride | Polyvinyl acetate | Vinyl acetate chloride co-polymers | Polyvinyl butyral | Polystyrene | "Epoxy" Resins | Polyacryliques-esters | Cellulose nitrates | Ethoxy cellulose | Cellulose acetates | Coumarone-indene resins |
|---|---|---|---|---|---|---|---|---|---|---|---|
| Benzene | | + | | | + | | + | | + | | + |
| Toluene | | + | | | + | | + | | + | | | + |
| Acetone | + | + | + | | + | + | + | + | + | + | + |
| Methylethylketone | + | + | + | | + | + | | + | + | | + |
| Methylisobutylketone | + | + | + | | + | + | | + | + | | + |
| Isophorone | + | + | + | + | + | + | | + | + | + | + |
| Methanol | | + | | + | | | | + | + | | |
| Ethanol | | | | + | | | | | + | | |
| Propanol | | | | + | | | | | + | | |
| Isopropanol | | | | + | | | | | + | | |
| Butanol | | | | + | | | | | + | | |
| 2-Ethoxy ethanol | | | | | | + | | + | + | | |
| Ethyl Acetate | | + | | | + | + | + | + | + | | + |
| Propyl Acetate | | + | | | + | + | + | + | + | | + |
| Isopropyl Acetate | | + | | | + | + | + | + | + | | + |
| Butyl Acetate | + | + | + | | + | + | + | + | + | | + |
| 2-Ethoxy ethyl Acetate | + | + | + | | + | + | + | + | + | | + |

All percentages given in this specification and claims are by weight unless expressly stated otherwise.

Other details of the invention are apparent from the following description.

In the accompanying drawings, given as non-limitative examples:

Figure 1:
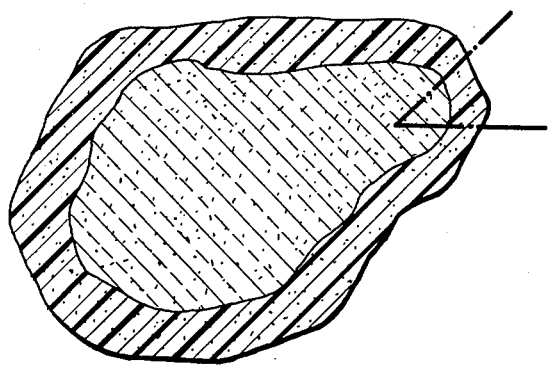
FIG. 1 shows on a large scale, in axial section, a granular product according to the invention, comprising a single layer of coated particles.

a granulator or mixer such as those currently used in industry (rotating drum, ribbon mixers, etc.). The granulator is set going and there is sprayed onto the nuclei 1, by means of an injector, a solution of the macromolecular resin in an organic anhydrous solvent, as mentioned hereinbefore. The granulator is allowed to turn at such speed (e.g. about 15 to 25 revolutions per minute) that the resin solution spreads uniformly over the surface of the nuclei 1, then there is added gradually, in the form of a fine powder, the mixture of water-soluble particles 4 and water-insoluble particles 5 and 6 to form part of the coating layer 2. The granulator is rotated for a period of substantially double the time necessary for the impregnation, in order to allow of an even distribution of the particles on the nuclei 1, and a certain smoothing of the coating layer. The granulator is then stopped and the contents discharged.

The granular products obtained are dried by known techniques such as heating under normal or reduced pressure at moderate temperature by infrared radiation or by the passage of a stream of gas, heated or not, this gas being, for example, air (e.g. of 70°). Heating temperatures should be below the softening point of the resin layer, to prevent agglomeration of granules.

According to a variant of the method of manufacture, the solution of macromolecular resin and the mixture of materials 4, 5 and 6 of the coating are simultaneously introduced, in small portions; a more or less large proportion of the resin solution can be introduced into a last batch to reinforce the solidity of the coating.

It can be advantageous to saturate the nuclei with the solvent used before spraying on the macromolecular resin solution; this is particularly useful when the nuclei are more or less porous.

During drying of the granular products, the resin solvent may be recovered by known means such as condensation or adsorption.

Figure 3:
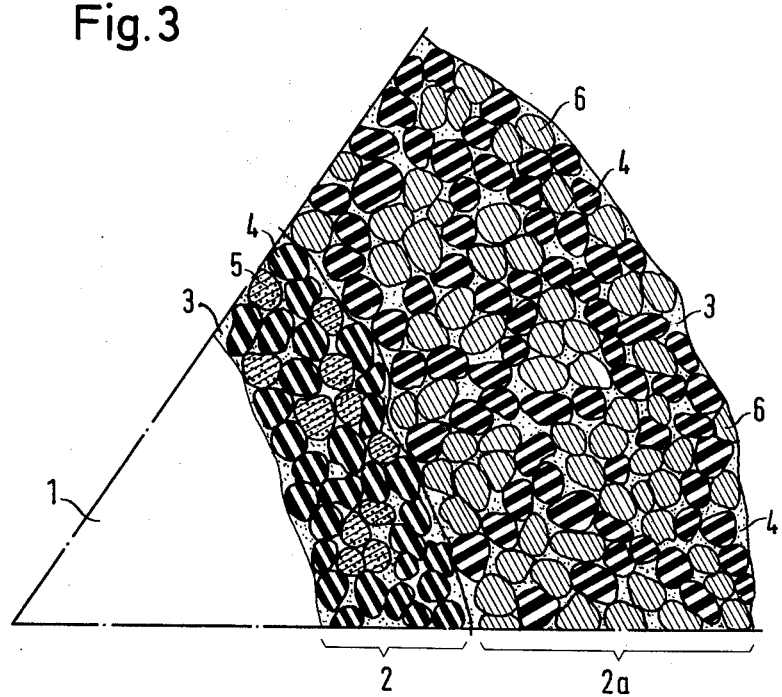
FIG. 3 is a sector of a section of a granular product having two successive different layers of coated particles.

In another embodiment shown in FIG. 3, the granular product differs from the first embodiment in that it comprises a second coating layer 2a; the coating layers 2 and 2a differ in the nature of the powder which they contain and/or in the nature of the macromolecular resins bonding the powders.

For instance, in the case of a nucleus made of a material which is incompatible with materials forming particles of the outer coating 2a, this first coating layer 2 can be an intermediary coating separating the nucleus and said outer coating.

To obtain the second coating layer 2a, one can simply change the nature of the powder while keeping the same resin solution; in this case it is not necessary to dry the granular product before applying the second coating layer 2a. On the other hand, if this second layer 2a necessitates a change of resin, it is preferably initially to dry the granular product, and to choose, for the second resin, a solvent which is a non-solvent for the first resin.

The granular products obtained according to this third embodiment, are permeable like those of the first embodiment and advantageously permit the location on the same nucleus 1 of several mutually imcompatible active materials.

However, the rapid access of moisture of the soil through both layers of the coating to the nucleus must also be guaranted by restricting the content of resin to the minimum necessary to hold particles of the layers and nucleus of the granule together while leaving enough interstices and contact areas between water-soluble particles to active the aforesaid end.

It is clearly evident that the granular product of the invention can undergo modifications relative to the particular examples described above, which do not fall outside the scope of the invention. Thus, in a more improved version, the nucleus 1 could receive more than two coating layers.

In particular, it is well known that products which contain sodium chlorate besides an organic material always present risks of spontaneous inflammation or even of explosion during handling or manufacture. Such incompatibility can easily be overcome by the interposition between the Na Cl O$_3$- containing nucleus and the outer coating which can contain organic materials, of an intermediary coating comprising a sufficient amount of incombustible preferably water-soluble substance, for instance potassium chloride.

Experience has shown that this practically avoids all risk of spontaneous inflammation or explosion.

A particularly interesting embodiment consists of a central nucleus comprising at least 25% by weight of sodium chlorate and at least 40% by weight of material which is soluble in water without decomposition, any residue being chosen from among solid and incombustible materials; the outer coating comprises particles of solid materials comprising at least one organic herbicide representing at least 15 percent by weight of this coating and at least one incombustible material, at least one of these solid materials being soluble in water and representing at least 40% by weight of the coating; the intermediary coating comprises particles of solid and incombustible material, at least one of these materials representing at least 40% by weight of this intermediary coating and being soluble in water without decomposition, these particles being bound together, to the central nucleus and to the outer coating by the same resin as that which is contained in the outer coating, the total amount of the resin in the final product being comprised between 0.1 and 2%, but not exceeding 10% of the weight of each the two layers of the coating.

In this case, the central nucleus may represent from 65 to 94% by weight of the product, the intermediary coating from 3 to 20% and the outer coating from 3 to 20% by weight.

Preferably the outer coating contains particles of a coloured organic pigment representing at the most 1% by weight of said coating.

The solid incombustible materials wnhich can be incorporated in the nucleus are preferably dried clay, brick, pumice-stone, calcium carbonate pyrophyllite, kaolin, dolomite, plaster, sodium chloride, sodium sulfate, sodium silicate and sodium borate. The particles of solid and incombustible materials which are soluble in water are, preferably, chosen from the soluble mineral salts of sulfuric acid, hydrochloric acid, hydrofluoric acid, hydrobromic acid, boric acid, fluoboric acid, carbonic acid, silicic acid, prussic acid, phosphoric acid, sulfamic acid, tungstic acid, molybdic acid and their mixtures.

The particles of non-combustible which are insoluble in water are, preferably, selected from kaolin, talcum, dried clay, brick, pumice-stone, magnesia, mica, pyrophyllite, dolomite, plaster, iron oxide, zinc oxide, titanium oxide, antimony oxide, cryolite, and the insoluble mineral salts of the above mentioned acids. The average greatest diameter of the solid particles contained in the outer coating and in the intermediary coating does not exceed 0.2 mm.

The average greatest diameter of the particles which are soluble in water is preferably comprised between 0,001 and 0.1 mm.

The outer coating can also contain particles of mineral or metallic pigments.

When the outer coating contains an organic pigment, it is preferably selected from those which are presenting a very weak solubility or which have no solubility at all in the used solvent or solvents and a high resistance to migration into the chosen resin.

The macromolecular resin used as binding agent is advantageously a homopolymer, a copolymer or a mixture of these polymers, each type of polymer being facultatively plastified.

Preferably the outer coating and the intermediary coating are each containing from 0.5 to 2% by weight of resin.

The same binders as previously mentioned are suitable for use as binders in the outer and intermediary coatings.

The resin or resins constituting the binder optionally contain one or more of the plasticisers cited, above, in the same proportions as already mentioned.

The particles or organic herbicide of the outer coating are preferably selected from herbicidal derivatives of phenoxyacetic acid, phenoxypropionic acid, phenoxybutyric acid, 4-amino-3,5,6-trichloro-picolinic acid, from s-triazine, from phenoxy-ethylsulfuric acid, halogenated benzoic acid, halogenated acetic acid, halogenated propionic acid, phenyl-urea, bipyridylium, 1,2,4-triazole, diazines, phenol, benzonitrile, thiocarbonyl, phenylcarbamic acid and thiocarbamic acids.

Generally preferred among these herbicidal products are:
the sodium salts and the potassium salts of
2,4-dichloro-phenoxyacetic acid,
4-chloro-2-methyl-phenoxyacetic acid,
2,4,5-trichloro-phenoxyacetic acid,
2-(4-chloro-2-methyl-phenoxy)-propionic acid,
2-(2,4-dichloro-phenoxy)-propionic acid,
2-(2,4,5-trichloro-phenoxy)-propionic acid,
4-(2,4-dichloro-phenoxy)-butyric acid,
4-(4-chloro-2-methyl-phenoxy)-butyric acid,
4-(2,4,5-trichloro-phenoxy)-butyric acid,
4-amino-3,5,6-trichloro-picolinic acid, and
0-(2,4-dichloro-phenoxy)-ethyl sulfuric acid;
also the free 2,3,6-trichlorobenzoic acid,
trichloroacetic acid, and
3,6-dichloro-2-methoxy-benzoic acid;
sodium chloroacetate,
sodium 2,2-dichloro-propionate,
sodium 2,2,3-trichloro-propionate,
N,N-dimethyl-N'-phenyl urea and the
trichloroacetate thereof,
N,N-dimethyl-N'-(4-chlorophenyl) urea trichloroacetate 5-amino-4-chloro-phenyl-3-pyridazone
5-bromo-6-methyl-3-sec butyl-uracile
1,1'-dimethyl-4,4'-bipyridylium dichloride bis 3,5-dimethyl-4-morpholinyl -
1,1'-acetyl-4,4'-bipyridylium-dichloride
9,10-dihydro-8a,10a-diaza-phenanthrene dibromide
2,3,5,6-tetrachloro-dimethyl terephtalate
sodium N-methyl-dithiocarbamate
3-amino-1,2,4-triazole
isopropyl-N-phenylcarbamate 2,4-dinitro-6-sec. butyl-phenol
2,6-dichloro-benzonitrile 3,5-dibromo-4-hydroxy-benzonitrile
2,6-dichloro-thiobenzamide
sodium isopropylxanthate
the s-triazines defined by the formula

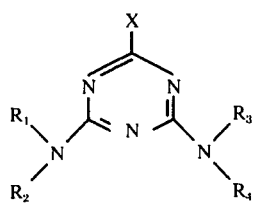

wherein X represents a chlorine atom or a methoxy group or a methylthio group and $R_1$, $R_2$, $R_3$ and $R_4$ being the same or different, each represents a hydrogen atom or an alkyl group of from 1 to 5 carbon atoms in straight or branched chain which can optionally bear a methoxy group as substituent; preferred s-triazines are the following:
2-chloro-4-ethylamino-6-tert.-butylamino-s-triazine
4-methylamino-6-sec. butylamino-2-methoxy-s-triazine
4-ethylamino-6-isopropylamino-2-methylthio-s-triazine
4-ethylamino-6-sec. butylamino-2-methoxy-s-triazine
4-ethylamino-6-sec. butylamino-2-methylthio-s-triazine
4-ethylamino-6-tert. butylamino-2-methylthio-s-triazine
4,6-bis(ethylamino) 2-methylthio-s-triazine
6-isopropylamino-4-methylamino-2-methylthio-s-triazine
4,6-bis-(isopropylamino)-2-methylthio-s-triazine
2-chloro-4-isopropylamino-6-ethylamino-s-triazine The average greatest diameter of the nucleus of the granular products according to this embodiment of the invention is preferably comprised between 0.6 and 16 mm and more preferably between 1 and 8 mm. The weight of the entire coating of the granules is preferably comprised between 6 and 35% or more preferably between 10 and 30% of the total weight of the granular product.

The average value of the greatest diameter of the granules in the product according to this embodiment of the invention, is thus generally comprised between about 0.6 to 20 mm and preferably between 1.0 and 10 mm.

The manufacture of the granular products according to this embodiment of the invention is made as previously described, and more particularly as described in Experiment E hereinafter.

The macromolecular resin is used in the form of a solution in a volatile anhydrous organic solvent. This solution preferably contains from 2 to 10% of macromolecular resin.

The solvents are preferably chosen from among those having a low boiling point and a high chlorine content such as, for instance, dichloromethane, chloroform, carbontetrachloride, trichloroethane, trichloroethylene, and perchloroethylene.

It is generally advantageous to soak the nuclei with the solvent to be used before proceeding to coat them; this avoids introducing the macromolecular resin, which is a combustible material, into the nuclei containing sodium chlorate.

The experiments hereinafter described permit the better understanding of the unexpectedly rapid action of products prepared according to the invention.

EXPERIMENT A

Into a sugar coater of type MG-2-P, made by the French company F. DUMOULIN + Cie. of La Varenne (Val de Marne), France, there was charged 40 kg of urea in spherical particles of diameter 2 ± 1 mm. By means of an injection tube, there were added, over about 20 minutes, 5 kg of a 4% solution in methylene chloride of high molecular weight polyvinyl acetate (see (f) infra); simultaneously there was introduced 9.8 kg of powder constituted as follows:

| | |
|---|---|
| sodium 2,4-dichlorophenoxyacetate | 5.00 kg, |
| Kaolin | 4.79 kg, and |
| coloured pigment insoluble in water | 0.01 kg. |

The drum of the sugar coater was kept rotating throughout the operation. The product was dried by passage in a current of hot air (70° C).

There were thus obtained granules the coating of which was spread very evenly over the whole of the surface of the beads of urea. It was observed after sieving that the proportion of powder not attached was practically nil; these granules are hereinafter denoted A-1.

The granules A-1 were placed in a column for measuring the liberation and constituted by a glass tube, located vertically, the lower portion of which was provided with a tube allowing precise regulation of the flow from the tube.

Into this column were introduced 5 g of coated granules between two tampons of glass wadding; 60 ml of distilled water was poured in from above and allowed to run out through the tap at the base at a rate of 415 microlitres per minute. At the end of one hour the liquid recovered was evaporated to dryness and the residue weighed; it was observed that the weight of this was 4.35 g, corresponding to the liberation of 96.6% of the soluble material contained in the granules A-1.

Variant A-2

By replacing the sodium 2,4-dichlorophenoxyacetate by sodium 4-chloro-2-methyl phenoxyacetate, there was obtained under the same conditions, a liberation of 4.45 g, i.e. 98.9% of the soluble materials contained in the granules A-2.

Variant A-3

By replacing half the sodijm 2,4-dichlorophenoxyacetate by kaolin, there was obtained, under the same condition, a liberation of 4.1 g, i.e. 96.5% of the soluble materials contained in the granules A-3.

Variant A-4

By replacing the whole of the sodium 2,4-dichlorophenoxyacetate by kaolin, there was obtained, under the same conditions, a liberation of 0.85 g, i.e. 21.2% of the soluble material contained in the granules.

Variant A-5

The 4% solution of polyvinylacetate used in case A-1 was replaced by an 8% solution of the same polymer, the other constituents remaining unchanged. The residue obtained operating in a column as described above was 3.5 g corresponding to liberation of 77.7% of the soluble material.

Variant A-6

By replacing the whole of the sodium 2,4-dichlorophenoxyacetate by kaolin and using an 8% polyvinylacetate solution, there was obtained granules giving under the conditions previously set forth, liberation of 0.45 g, i.e. 11.2% of the soluble material.

Variant A-7

Uncoated beads of urea were placed in the column; operating in the same fashion, a residue of 4.85 g was obtained, corresponding to liberation of 97% of the soluble material.

This experiment shows how rapidly the liberation of soluble material from the granular products of the invention actually takes place; liberation percentages are obtained with granules coated with a 4 % solution of polyvinyl acetate (A-1, A-2, A-3), which are practically identical to those obtained when using noncoated granules (A-7). This is still the case even if the soluble powder contained in the coating only represents 5 % of the total weight of the granule (A-3); in fact the speed of liberation is still very large when the proportion of insoluble binder is raised to 8 % (A-5); in contrast, the liberation speed is very weak, even with a very small proportion of binder, when the coating powder does not contain soluble material (A-4 and A-6).

EXPERIMENT B

The solidity of the coating of granules A-1 prepared as described above was tested in the following manner. Into a 250 ml glass flask there were introduced 100 g of coated granules; the closed flask was fixed on a shaker adjusted to 150 oscillations per minute; at the end of 30 minutes, the contents of the flask was placed on a 100 micron sieve, and the quantity of powder passed through was weighed; the weight ratio between this quantity of powder and that fixed on the nuclei was 0.25:100.

There were prepared in the same manner a large number of coated granules, in particular the following (values expressed in parts by weight of the final coated granule):

TABLE II

| NUMBER | 1 | 2 | 3 | 4 | 5 | 6 | 7 | 8 | 9 | 10 |
|---|---|---|---|---|---|---|---|---|---|---|
| Nucleus: | | | | | | | | | | |
| Urea beads | 80 | — | — | — | 80 | 80 | 76 | — | — | — |
| Fertiliser compound, NPK 7/15/30 | — | 86 | 82 | 80 | — | — | — | — | — | — |
| Sodium chlorate | — | — | — | — | — | — | — | 80 | 80 | 80 |
| Powder: | | | | | | | | | | |
| Kaolin | 9.6 | 6.8 | 5.7 | 9.7 | 9.5 | 9.7 | 9.6 | 5.5 | 5.5 | 5.3 |
| Potassium nitrate | — | — | — | 10 | — | — | 14 | — | — | — |
| Magnesium sulphate | — | — | 12 | — | 10 | 10 | — | — | — | — |
| Ammonium sulphate | 10 | 7 | — | — | — | — | — | — | — | — |
| 2-chloro-4-ethylamino-6-ter-butylamino-s-triazine | — | — | — | — | — | — | 4 | 4 | — | 2 |
| 4-ethylamino-6-sec.butyl-amino-2-methoxy-s-triazine | — | — | — | — | — | — | — | — | 4 | 2 |
| Sodium chloride | — | — | — | — | — | — | — | 10 | 10 | 10 |
| Binder: | | | | | | | | | | |
| High molecular weight poly- | | | | | | | | | | |

TABLE II-continued

| NUMBER | 1 | 2 | 3 | 4 | 5 | 6 | 7 | 8 | 9 | 10 |
|---|---|---|---|---|---|---|---|---|---|---|
| vinyl acetate(f) | 0.4 | 0.2 | 0.3 | 0.3 | 0.5 | 0.3 | 0.4 | 0.5 | 0.5 | 0.5 |

The solidity of the coatings of thus prepared granules was measured in a shaker under the conditions described above. The results, expressed as a percentage between the quantity of powder detached by shaking and that attached to the nucleus, were obtained as follows:

| 1 | 2 | 3 | 4 | 5 | 6 | 7 | 8 | 9 | 10 |
|---|---|---|---|---|---|---|---|---|---|
| 0.45 | 0.10 | 0.25 | 0.30 | 0.10 | 0.25 | 0.35 | 0.45 | 0.25 | 0.35 |

This experiment shows to what degree the coatings made according to the invention are solid: after 9000 shocks, the quantities of powder detached from the coating are in effect, in all cases, less than half of one percent.

Experiment C

Coated granules were prepared following the technique described above and using the following raw materials.

| Nucleus: | Urea beads | 25.49% |
|---|---|---|
| | Granules of fertiliser compound (NPK=7/15/30) | 27.36% |
| | Granules of fertiliser compound (NPK=16/20/0) | 30.75% |
| Coating: | Ammonium sulphate | 8.26% |
| | Kaolin | 7.88% |
| | High molecular weight polyvinylacetate | 0.26% |

There were thus obtained coated granules, titrating at 20.4% nitrogen, 10.2% phosphorus calculated as $P_2O_5$ and 8.2% of potassium calculated as $K_2O$.

These granules were used during the course of one summer, as fertiliser on areas of regularly watered lawn. The dosage used was 25 g per sq. meter. Other areas were treated simultaneously with a mixture comprising the same quantity in weight per square meter of ammonium sulphate and non-coated nuclei as noted above.

A third group of areas of the same lawn were not treated so as to serve as control.

Growth and colour of the turf of each group of areas were observed during the first 10 days; on the two groups of treated areas, more rapid growth and more intense green colouration than on the untreated areas were observed; no significant difference in growth or colouration between the two groups of treated areas.

This experiment shows that the action of the soluble materials of the coated granules according to the invention is not retarded compared to the same materials uncoated.

Experiment D

Coated granules were prepared following the technique previously described and using the following raw materials;

| Nucleus: | potassium chlorate | 80% |
|---|---|---|
| Coating: | 3-amino-1,2,4-triazole | 2% |
| | 4-ethylamino-6-sec.butylamino-2-methoxy-5-triazine | 2% |
| | kaolin | 5.5% |
| | sodium chloride | 10% |
| | high molcular weight polyvinyl acetate | 0.5% |

The so prepared coated granules were used as total herbicide at a dose of 20 g/m² in the GARDOUCH region (Haute Garonne) in France and readings were taken periodically to discover the progress of the herbicidal action. The results taken at 10, 20, 30, 60 and 90 days are shown in the table below. Marks were given from 0-10, 0 indicating no action and 10 a total absence of vegetation.

| 10 days | 20 days | 30 days | 60 days | 90 days |
|---|---|---|---|---|
| 6 | 8 | 9 | 9 | 9 |

These results show that the shock action due to the sodium chlorate in the nucleus and to the aminotriazole in the coating is effective from the tenth day at least; this action is then applied and relayed by the triazine derivative which gives the composition a remanent effect, whereby the absence of a vegetation covering is still almost total after at least three months, while it is known that the sodium chlorate and the aminotriazole only have a very weak remanence, and that, on the other hand, the triazine derivatives in contrast to the previous compounds, have no shock action.

Experiment E

In order to obtain the granular product of this experiment there was used an apparatus called "Nauta Perfect" made by the Dutch Company of NAUTAMIX N.V. of Haarlem, constituting of a conical cistern of 100 liters provided in its interior with an Archimedean screw rotating on itself and moving along the generating lines of the cistern.

Granules titrating 88% by weight of sodium chlorate, the balance being dried clay, and having an average largest diameter of from about 1 to 1.5 mm were introduced into this apparatus.

The weight of these granules destined to be the nuclei of the final product was calculated to obtain 30 kg of the final granular product, the compositon of which is given hereafter.

In order to apply the intermediary coating, the nuclei were impregnated with 5% of their weight of methylene chloride whereafter there was simultaneously introduced into the cistern a first coating powder, in a proportion and according to a composition as given hereafter, and a 4% by weight-solution polyvinyl acetate in methylene chloride in an amount corresponding to 40% of the coating.

The Archimedean screw was maintained working during the whole operation; the final products were then dried by a stream of warm air.

Another series of final products, without intermediary coating was prepared in the same manner. The products thus prepared had the following constituents (amounts given in parts by weight).

TABLE III

|  |  | A-1 | A-2 | B-1 | B-2 | C-1 | C-2 | D-1 | D-2 | E-1 | E-2 | F-1 | F-2 | G-1 | G-2 | H-1 | H-2 | I-1 | I-2 |
|---|---|---|---|---|---|---|---|---|---|---|---|---|---|---|---|---|---|---|---|
| Intermediary coating | Kaolin | — | 7,6 | — | 7,5 | — | 7,5 | — | 7,5 | — | 8 | — | 12 | — | 8 | — | 12 | — | 5 |
| | Sodium chloride | — | 7,5 | — | 7,5 | — | 7,5 | — | 7,5 | — | — | — | — | — | — | — | — | — | — |
| | Sodium carbonate($a_1$) | — | — | — | — | — | — | — | — | — | — | — | — | — | — | 8 | — | — | — |
| | Borax | — | — | — | — | — | — | — | — | — | — | — | — | — | 12 | — | — | — | — |
| | Sodium fluoroborate | — | — | — | — | — | — | — | — | — | 12 | — | 3 | — | — | — | — | — | — |
| | sodium silicate | — | — | — | — | — | — | — | — | — | — | — | — | — | — | — | — | — | 5 |
| Outer coating | Kaolin | 2 | 2 | 3 | 3 | 3 | 3 | — | — | 4 | 4 | 2 | 2 | 2 | 2 | — | — | 1 | 1 |
| | Sodium chloride | 2 | 2 | 2 | 2 | 2 | 2 | 2 | 2 | — | — | — | — | — | — | — | — | — | — |
| | Sodium fluoride | — | — | — | — | — | — | — | — | — | — | 3 | 3 | — | — | — | — | — | — |
| | Sodium carbonate($a^1$) | — | — | — | — | — | — | — | — | — | — | — | — | — | — | 3 | 3 | — | — |
| | Sodium sulfate($a_1$) | — | — | — | — | — | — | — | — | — | — | — | — | — | — | — | — | 1,5 | 1,5 |
| | 3-amino-1,2,4-triazole | 6 | 6 | — | — | — | — | — | — | 8 | 8 | — | — | — | — | — | — | — | — |
| | MCPA($b_1$) | — | — | 5 | 5 | — | — | — | — | — | — | 8 | 8 | — | — | — | — | — | — |
| | 2,4-D-Na($c_1$) 2-chloro-4-ethylamino 6-tertiobutyl-amino-s-triazine | — | — | — | — | 5 | 5 | — | ;13 | — | — | — | — | 5 | 5 | — | — | — | — |
| | | — | — | — | — | — | — | 8 | 8 | — | — | — | — | — | — | 10 | 10 | 4 | 4 |
| Polyvinyl acetate(f) | | 0,16 | 0.28 | 0,28 | 0,28 | 0,16 | 0.28 | 0,16 | 0,28 | 0,19 | 0,35 | 0,21 | 0,33 | 0,1 | 0,28 | 0,21 | 0,37 | 0,10 | 0,18 |
| Nucleus | | Balance to 100 | | | | | | | | | | | | | | | | | |

($a_1$)hydrated salt
($b_1$)abbreviation of 4-chloro-2-methyl-phenoxyacetic acid
($c_1$)abbreviation of the sodium salt of 2,4-dichloro-phenoxyacetic acid
(f)high molecular weight polyvinylacetate having a molecular weight of 35–40.000 and a melting range of 180 ± 10° C, produced by the French firm of RHONE-POULENC of Paris, under the Trade Mark RHODOPAS HH. The solution is used at 5% in acetone or 4% in methylene chloride.

The sensitivity to the shock of the granular products thus prepared was tested in a device described in the International Regulation for the transport of dangerous merchandises (R.I.D) under the marginal reference 1155b; this device comprises an anvil which is struck by a steel ram having a weight of 3.5 kg sliding between two vertival bars; a solid mass of concrete is attached to the anvil; the ram moves in front of a graduated ruler and is held in high position at a chosen level by means of an electro-magnet; 100 g of the granular product to be tested, previously dried during one hour in a drying-chamber at 90° C, are wrapped in an aluminum-foil; the small package which is thus obtained is placed on the anvil at the center of the area to be fit by the ram; the ram is then released by switching off current flow through the electromagnet, and hits the product. The number of detonations is noted.

Table IV below shows for every tested product the dropping weight of the ram in centimeters and the number of detonations which have occurred.

TABLE IV

| Tested product | Height | Number of tests | Number of detonations |
|---|---|---|---|
| A-1 | 100 | 15 | 12 |
| A-2 | 100 | 15 | 0 |
| B-1 | 100 | 15 | 13 |
| B-2 | 100 | 15 | 0 |
| C-1 | 120 | 10 | 5 |
| C-2 | 120 | 10 | 0 |

TABLE IV-continued

| Tested product | Height | Number of tests | Number of detonations |
|---|---|---|---|
| D-1 | 100 | 10 | 8 |
| D-2 | 100 | 10 | 0 |
| E-1 | 90 | 15 | 7 |
| E-2 | 90 | 22 | 0 |
| F-1 | 90 | 19 | 16 |
| F-2 | 90 | 20 | 0 |
| G-1 | 110 | 15 | 7 |
| G-2 | 110 | 20 | 0 |
| H-1 | 100 | 15 | 13 |
| H-2 | 100 | 20 | 0 |
| I-1 | 100 | 18 | 11 |
| I-2 | 100 | 25 | 0 |

Non-limitative examples will now be given of certain methods of performing the invention, with the sole object of illustrating the manifold possible granular products obtainable and of allowing better understanding of what has gone before.

EXAMPLE 1

Into a sealed horizontal rotating drum of 2000 liters were charged 818 kg of fertiliser granules having an average diameter of 3 mm and an NPK formula of 10/16.6/20, made up as follows:
  0.34% nitrogen - from potassium nitrate
  9.66% nitrogen from ammonium sulphate and phosphate
  16 % $P_2O_5$ from ammonium phosphate
  0.67% $P_2O_5$ from dicalcium phosphate
  1.06% $K_2O$ from potassium nitrate
  18.97% $K_2O$ from potassium sulphate The drum is set in rotation at a speed of about 20 revolutions per minute and, by means of an injector, 20 kg of a 5% solution of high molecular weight polyvinyl acetate (see (f) infra) in acetone is introduced. The drum is allowed to turn for 10 minutes to obtain good distribution of the solution on the surface of the granules and there is then added at a rate of 10 kg per minute, 100 kg of powder made up as follows:

| | |
|---|---|
| magnesium sulphate | 66.85% |
| ferric chelate ETPA(a) | 0.45% |
| kaolin | 31.37% |
| manganese sulphate | 0.30% |
| nickel sulphate | 0.06% |
| zinc sulphate | 0.08% |
| copper sulphate | 0.08% |
| sodium borate | 0.70% |
| Rubis Lutetia RL(b) | 0.15% |

(a)ferric chelate of sodium diethylenetriaminopentacetate, made by the applicant under the trade mark SEQUESTRENE 330.
(b)pigment made by the Compagnie Francaise des Matieres Colorantes S.A.

Then another 20 kg of the aforesaid acetonic solution of polyvinyl acetate and finally another 79.5 kg of the above powder are added and rotation is continued for 20 minutes. The contents of the drum are then poured into a hot air drying column (55–60° C); the product obtained appears as rose-coloured granules corresponding to FIG. 2, and constitutes a fertiliser having a formula NPK of 8/13/16, rich in magnesium and particularly useful for roses.

The solidity of the coating layer is tested as follows: 100 g of product are introduced into a 100 ml glass flask; the closed flask is fixed on a vibrator set at 150 oscillations per minute. At the end of half an hour, the material is sieved and the quantity of powder detached from the coating: this quantity is zero or very small, and always less than 0.5% by weight of the powder used for the coating.

The dissolution speed of the product is measured as follows: in a 30 mm diameter glass column provided at its lower end with a tap, there are placed 5 g of the product between two layers of glass wool; there is placed above the whole a bed of infusorial earth known under the name of CELITE type FC. A stream of water is made to pass from top to bottom of the column and the outflow speed adjusted to 500 microliters per minute. At the end of an hour, the water collected is evaporated to dryness; dissolution of 1.53 g of product is noted, i.e. 30.6%.

If the 5% solution of polyvinylacetate is replaced by a 7% solution of the same resin, the dissolution is again equal at 28.7%. With a 10% solution, dissolution remains very fast (20.6%).

In the same conditions the dissolution rate of the nuclei used, not coated, is 32% at the hour.

Examples 2 – 12

Figure 2:
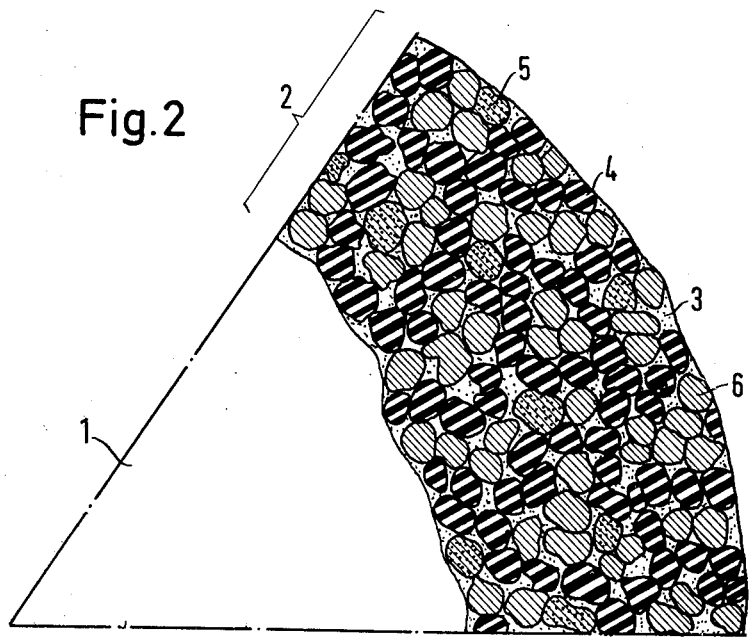
FIG. 2 is a sector, on a larger scale, of the section shown in FIG. 1, showing the structure of the coating; with the water-soluble particles forming a continuous network.

Operating as noted in Example 1 and using the raw materials noted below, granules corresponding to FIG. 2 are obtained which are fertiliser compounds of rapid action. Values are expressed in parts by weight throughout.

TABLE V

| Example Number | 2 | 3 | 4 | 5 | 6 | 7 | 8 | 9 | 10 | 11 | 12 |
|---|---|---|---|---|---|---|---|---|---|---|---|
| Nucleus | | | | | | | | | | | |
| Fertiliser compound 7/15/30-S(c) | — | 61.6 | 27.4 | 55.7 | 54.3 | — | — | 22.7 | 47.9 | — | 71.0 |
| Fertiliser compound 16/20/0(d) | 46.2 | — | 30.7 | 24.7 | 27.5 | 45.8 | — | — | 32.1 | — | — |
| Urea beads | 28.6 | 19.5 | 25.5 | — | — | 29.2 | 76.0 | 11.8 | — | 61.0 | — |
| Coating powder | | | | | | | | | | | |
| Magnesium sulphate | — | — | — | — | 12.0 | — | 11.0 | — | 10.0 | — | — |
| Triammonium phosphate | — | — | — | — | — | — | — | — | — | 27.0 | 13.5 |
| Ferric chelate ETPA(a) | 0.1 | — | 0.1 | 0.2 | 0.08 | — | 12.0 | 0.2 | — | — | — |
| Ferric chelate EDDHA(e) | — | 10.0 | — | — | — | — | — | — | 2.0 | — | 6.0 |
| Manganese sulphate | — | — | — | — | 0.05 | — | — | — | — | 0.1 | — |
| Nickel sulphate | — | — | — | — | 0.01 | — | — | — | — | 0.02 | — |
| Zinc sulphate | — | — | — | — | 0.01 | — | — | — | — | 0.04 | — |
| Copper sulphate | — | — | — | — | 0.01 | — | — | — | — | 0.05 | — |
| Sodium borate | 0.2 | — | — | 0.2 | 0.13 | — | — | — | — | — | — |
| Boric acid | — | — | — | — | — | — | — | — | — | 0.4 | — |
| Ammonium sulphate | — | — | 8.3 | — | — | 4.3 | — | 6.0 | — | — | — |
| Potassium nitrate | 13.5 | — | — | 9.8 | — | 10.0 | — | 8.0 | — | — | — |
| Sodium molybdate | 0.2 | — | — | 0.08 | — | 0.1 | — | — | — | — | — |
| Kaolin (inert filler) | 10.7 | 8.0 | 7.64 | 9.03 | 5.62 | 10.0 | — | 8.45 | 7.65 | 10.9 | — |
| Dried clay | — | — | — | — | — | — | — | — | — | — | 7.0 |
| Cyanine Lutetia solid B(p) | 0.1 | 0.15 | — | — | — | 0.05 | — | 0.06 | — | — | — |
| Carbon black | — | 0.4 | — | — | — | — | — | — | — | — | 2.0 |
| Solid yellow Vulcan GR(n) | — | — | — | 0.04 | — | — | 0.03 | — | — | 0.04 | — |
| Phthalocyanine green PV O 1(j) | — | — | 0.1 | — | — | — | 0.07 | 0.04 | — | — | — |
| Red Lutetia solid 5 BO(k) | — | — | — | — | 0.04 | 0.05 | — | — | — | — | — |
| Bordeaux Irgacete GL(m) | — | — | — | — | — | — | — | — | 0.1 | — | — |
| Coating binder | | | | | | | | | | | |
| Polyvinyl acetate(f) | 0.4 | 0.35 | 0.26 | 0.25 | 0.25 | — | — | 0.30 | — | — | — |
| Vinyl acetate-vinyl chloride copolymer(g) | — | — | — | — | — | 0.5 | 0.9 | 0.15 | — | — | — |
| Polystyrene(h) | — | — | — | — | — | — | — | — | 0.25 | — | 0.5 |
| Ethoxy cellulose(i) | — | — | — | — | — | — | — | — | — | 0.36 | — |
| Ethyl phthlate | — | — | — | — | — | — | — | — | — | 0.09 | — |

(c)granules of watersoluble fertiliser produced by the French firm POTASSE & ENGRAIS CHIMIQUES, of Paris, comprising the following fertilising materials:

| | |
|---|---|
| nitrogen from ammonium phosphate | 0.5% |
| nitrogen from ammonium phosphate and sulphate | 6.5% |
| phosphorous from ammonium phosphate | 14.0 (as $P_2O_5$) |
| phosphorous from dicalcium phosphate | 1.0% (as $P_2O_5$) |
| potassium from potassium nitrate | 1.6% (as $K_2O$) |
| potassium from potassium sulphate | 28.4% (as $K_2O$). |

(d)granules of watersoluble fertiliser produced by the French firm of Ugine - Kuhlmann, of Paris, comprising the following fertiliser materials:

| | |
|---|---|
| nitrogen from ammonium sulphate | 12% |

TABLE V-continued

| Example Number | 2 | 3 | 4 | 5 | 6 | 7 | 8 | 9 | 10 | 11 | 12 |
|---|---|---|---|---|---|---|---|---|---|---|---|
| nitrogen from ammonium phosphate | 4% | | | | | | | | | | |
| phosphorus from ammonium phosphate | 20% (as $P_2O_5$). | | | | | | | | | | |

(e) ferric chelate of di-(sodium 2-hydroxy phenylacetate) ethylene diamine produced by the applicant under Trade Mark SEQUESTRENE 138.
(g) copolymer of vinyl chloride (85%) and vinyl acetate (15%) produced by the firm of RHONE-POULENC. A solution of 4% in methyl ethyl ketone or trichloroethylene is used.
(h) non-modified polystyrene used in 3% solution in methylene chloride.
(i) a compound is used having an ethoxy rating between 48.5 and 49% by weight and in the form of a 4% solution in methylene chloride or in methanol. When ethyl phthalate is used, this is added to the preceding solution.
(j) chlorinated copper phthalocyanine, produced by the French firm, POTASSE & ENGRAIS Chimiques.
(k) complex mixture of calcium and manganese oxynitrates made by the applicant.
(m) complex of cobalt oxynitrate made by the applicant.
(n) diazo pigment derived from benzidine made by the German firm of HOECHST, Frankfurt.

(p) copper phthalocyanine made by Compagnie Francaise des Matieres Colorantes.

EXAMPLES 13 – 22

Operating as stated in Example 1 and using the raw materials noted below, granules corresponding to FIG. 2 are obtained which are herbicides with a very wide spectrum of "total herbicidal effect" in which the shock action is given by the sodium chlorate of the nucleus and, optionally, by the 3-amino-1,2,4-triazole of the coating, the persistence being ensured by one or more derivatives of sym. triazine. Values are expressed in parts by weight.

EXAMPLES 23 – 29

Operating as stated in Example 1 and using the raw materials noted below, granules corresponding to FIG. 2 are obtained which are total herbicides in which the shock action of the sodium chlorate constituting the nucleus is enhanced by the 4-amino-3,5,6-trichloropicolinic acid of the coating, persistence being ensured by one or more derivatives of sym. triazine. Values are expressed in parts by weight.

TABLE VI

| Example Number | 13 | 14 | 15 | 16 | 17 | 18 | 19 | 20 | 21 | 22 |
|---|---|---|---|---|---|---|---|---|---|---|
| Nucleus | | | | | | | | | | |
| Sodium chlorate | 83 | 83 | 77 | 77 | 80 | 80 | 80 | 80 | 80 | 80 |
| Coating powder | | | | | | | | | | |
| 3-amino-1,2,4-triazole | 2 | 2 | — | 2 | — | 2 | — | 2 | — | 2 |
| 2-chloro-4-ethylamino-6-terbutyl-amino-sym.triazine | — | — | 4 | 4 | — | — | 2 | 2 | 2 | 2 |
| 4-ethylamino-6-sec.butylamino-2-methoxy-sym.triazine | 2 | 1 | — | — | 4 | 4 | 2 | 2 | 1 | 1 |
| 6-sec.butylamino-2-methoxy-4-methyl-amino-sym.triazine | — | 1 | — | — | — | — | — | — | 4 | 4 |
| Methylthiotriazine(q) | — | — | 2 | 2 | — | — | — | — | — | — |
| Sodium chloride | 8 | 8 | 10 | 8 | 10 | 8 | 10 | 8 | 10 | 8 |
| Kaolin or dried clay | 4.6 | 4.6 | 6.5 | 6.5 | 5.5 | 5.5 | 5.5 | 5.5 | 5.5 | 5.5 |
| Coating binder | | | | | | | | | | |
| Polyvinyl acetate(r) or Vinyl acetate - vinyl chloride copolymer(s) | 0.4 | 0.4 | 0.5 | 0.5 | 0.5 | 0.5 | 0.5 | 0.5 | 0.5 | 0.5 |

(q) there is used one of the following compounds or a mixture containing two or more of these compounds:
4,6-bis(isopropylamino)-2-methylthio-sym.triazine
6-isopropylamino-4-methylamino-2-methyltho-sym.triazine
4,6-bis(ethylamino)-2-methylthio-sym.triazine
4-ethylamino-6-isopropylamino-2-methylthio-sym.triazine
4-ethylamino-6-sec.butylamino-2-methylthio-sym.triazine
(r) the product defined under (f) is used in 8% solution in acetone or methylene chloride
(s) the product defined under (g) is used in solution solution in methyl ethyl ketone or trichlorethylene.

TABLE VII

| Example Number | 23 | 24 | 25 | 26 | 27 | 28 | 29 |
|---|---|---|---|---|---|---|---|
| Nucleus | | | | | | | |
| Sodium chlorate | 79 | 85 | 85 | 79 | 79 | 79 | 79 |
| Coating powder | | | | | | | |
| Pichloram(t), potassium salt | 0.05 | 0.1 | 0.1 | 0.05 | 0.05 | 0.05 | 0.05 |
| 2-chloro-4-ethylamino-6-butyl-amino-sym.triazine | 4 | — | — | — | — | 2 | 2 |

TABLE VII-continued

| Example Number | 23 | 24 | 25 | 26 | 27 | 28 | 29 |
|---|---|---|---|---|---|---|---|
| 4-ethylamino-6-sec.butylamino-2-methoxy-sym.triazine | — | 2 | 1 | 4 | 2 | 2 | 1 |
| 6-sec.butylamino-2-methoxy-4-methylamino-sym.triazine | — | — | 1 | — | 2 | — | 1 |
| Methylthiotriazine(q) | 1 | — | — | — | — | — | — |
| Sodium chloride | 10 | 8 | 8 | 10 | 10 | 10 | 10 |
| Kaolin or dried clay | 5.45 | 4.5 | 4.5 | 5.45 | 5.45 | 5.45 | 5.45 |
| Coating binder | | | | | | | |
| Polyvinyl acetate(r) or vinyl chloride acetate copolymer(s) | 0.5 | 0.4 | 0.4 | 0.5 | 0.5 | 0.5 | 0.5 |

(t)common name of 4-amino-3,5,6 trichloropicolinic acid. The potassium salt is used.

EXAMPLES 30 – 37

Operating as stated in Example 1 and using the raw materials noted below, granules corresponding to FIG. 2 are obtained, which are total herbicides in which the nucleus contains one or more soluble active materials, and inert materials, soluble or insoluble. Values are expressed in parts by weight.

EXAMPLES 38 – 43

Operating as stated in Example 1 and using the raw materials noted below, granules corresponding to FIG. 2 were obtained, which constituted selective herbicides for market garden use, the nucleus of which contains one or more herbicidal materials, a fertiliser and a material of nematocidal and fungicidal action; the coating layer contains a complementary agent, which can be a fertilising or antichlorotic material. Values are expressed in parts by weight.

TABLE IIX

| Example Number | 30 | 31 | 32 | 33 | 34 | 35 | 36 | 37 |
|---|---|---|---|---|---|---|---|---|
| Nucleus | | | | | | | | |
| Sodium chlorate | 65 | 60 | 40 | 40 | 33 | — | — | 70 |
| Sodium chloride | — | — | 30 | 33 | 33 | 30 | 20 | — |
| 3-amino-1,2,4-triazole | — | — | — | — | — | — | 10 | — |
| Methylthiotriazine(q) | — | — | — | — | — | 10 | 10 | — |
| 2-chloro-4-ethylamino-6-terbutylamino-sym.triazine | — | — | — | — | — | 20 | 20 | — |
| Dried clay | 18 | 17 | 15 | 15 | 17 | 16 | 18 | 17 |
| Coating powder | | | | | | | | |
| 3-amino-1,2,4-triazole | 2 | — | 1 | — | 2 | 10 | — | 2 |
| 2-chloro-4-ethylamino-6-terbutylamino-sym.triazine | 4 | 4 | 2 | 2 | 4 | — | — | 4 |
| Methylthiotriazine(q) | 2 | 2 | 1 | 1 | 2 | — | — | 2 |
| Sodium chloride | 10 | 10 | 12 | 12 | 10 | 8 | — | — |
| Kaolin or dried clay | 6.5 | 6.5 | 6.5 | 6.5 | 6.5 | 5.2 | 6.6 | — |
| Sodium 2,4-dichlorophenoxyacetate | — | — | — | — | — | — | 15 | 4.7 |
| Coating binder | | | | | | | | |
| Polyvinyl acetate(r) or Vinyl acetate - chloride | 0.5 | 0.5 | 0.5 | 0.5 | 0.5 | 0.8 | 0.4 | 0.3 |

TABLE IX

| Example Number | 38 | 39 | 40 | 41 | 42 | 43 |
|---|---|---|---|---|---|---|
| Nuecleus | | | | | | |
| 4,6-bis(isopropylamino)-2-methylthio-sym.triazine | 0.2 | 0.2 | — | — | 0.2 | 0.2 |
| 4-ethylamino-6-terbutylamino-2-methyl-sym.triazine | — | — | 0.2 | 0.2 | — | — |
| Potassium nitrate | 8 | 8 | 8 | 8 | — | — |
| Triammonium phosphate | 13 | 13 | 13 | 13 | 15 | 15 |
| Potassium sulphate | 15 | 15 | 15 | 15 | 18 | 18 |
| Sodium bicarbamate | 50 | 50 | 50 | 50 | 45 | 45 |
| Dried clay | 6 | 7 | 6 | 7 | 5 | 5 |
| Coating powder | | | | | | |
| Potassium nitrate | — | — | — | — | 10 | 12 |
| Ferric chelate EPTA(a) | 4 | — | 4 | — | — | — |
| Ferric chelate EDDHA(e) | — | 3 | — | 3 | 2 | 4 |
| Sodium borate | — | — | — | — | 0.2 | 0.2 |
| Sodium molybdate | — | — | — | — | 0.1 | 0.1 |
| Carbon black | 0.2 | 0.2 | 0.2 | 0.2 | 0.2 | — |
| Kaolin | 3.3 | 3.3 | 3.3 | 3.3 | 3.9 | — |
| Coating binder | | | | | | |
| Polyvinyl acetate(f) or Vinyl acetate-vinyl chloride | | | | | | |

TABLE IX-continued

| Example Number | 38 | 39 | 40 | 41 | 42 | 43 |
|---|---|---|---|---|---|---|
| Copolymer(g) | 0.3 | 0.3 | 0.3 | 0.3 | 0.4 | 0.5 |

EXAMPLES 44 – 53

Operating as stated in Example 1 and using the raw materials noted below, granules according to FIG. 2 are obtained in which the nucleus comprises a soil fertiliser partly soluble in water, while the coating comprises a selective herbicide or an antichlorotic material. Values are in weight percent.

EXAMPLES 54 – 62

Operating as stated in Example 1 and using the raw materials noted below, granules corresponding to FIG. 2 are obtained in which the nucleus comprises a soil fertiliser, partly or wholly water soluble, and a complementary active material which can be an insecticide, a nematocide or a fungicide, the coating comprising a

TABLE X

| Example Number | 44 | 45 | 46 | 47 | 48 | 49 | 50 | 51 | 52 | 53 |
|---|---|---|---|---|---|---|---|---|---|---|
| Nucleus | | | | | | | | | | |
| Potassium nitrate | — | — | — | — | — | 12 | 12 | — | — | 6 |
| Triammonium phosphate | — | — | — | — | — | 25 | 25 | 30 | 30 | 12.5 |
| Potassium sulphate | — | — | — | — | — | 30 | 30 | 37 | 37 | 15 |
| Fertiliser compound 10/10/20 | 90 | 93 | 82 | 84 | 84 | — | — | — | — | — |
| Dried clay(u) | — | — | — | — | — | 23 | 26 | 17 | 18 | 50.5 |
| Coating powder | | | | | | | | | | |
| Ferric chelate ETPA(a) | 3 | — | — | — | — | 3 | — | — | — | — |
| Ferric chelate EDDHA(e) | — | 2 | 2 | 2 | 2 | — | 2 | 2 | — | 2 |
| 4,6-bis(isopropylamino)-2-methylthio-sym.triazine | — | — | — | 0.4 | — | — | — | 0.4 | — | 0.4 |
| 4-ethylamino-6-terbutyl-amino-2-methylthio-sym.triazine | — | — | — | — | 0.4 | — | — | — | 0.4 | — |
| Carbon black | 0.2 | 0.1 | 0.1 | 0.1 | 0.1 | 0.2 | 0.1 | 0.1 | — | 0.1 |
| Potassium nitrate | — | — | 8.2 | 6.8 | 6.8 | — | — | 6.8 | 8.2 | 6.8 |
| Kaolin | 6.5 | 4.7 | 7.3 | 6.3 | 6.3 | 6.5 | 4.7 | 6.3 | — | 6.3 |
| Ammonium sulphate | — | — | — | — | — | — | — | — | 6.1 | — |
| Coating binder | | | | | | | | | | |
| Polyvinyl acetate(r) or Vinyl acetate - chloride copolymer(s) | 0.3 | 0.2 | 0.4 | 0.4 | 0.4 | 0.3 | 0.2 | 0.4 | 0.3 | 0.4 |

(u)Granules of partly water soluble fertiliser produced by the French firm of POTASSE & ENGRAIS CHIMIQUES, Paris, comprising the following fertilising materials:

| | |
|---|---|
| nitrogen from potassium nitrate | 5% |
| nitrogen from potassium nitrate | 5% |
| phosphorus from bicalcium phosphate | 9.4% (as $P_2O_5$) |
| phosphorus from tricalcium phosphate | 0.6% (as $P_2O_5$) |
| potassium from potassium chloride | 3.2% (as $K_2O$) |
| potassium from potassium nitrate | 16.8% (as $K_2O$) | selective herbicide or an antichlorotic material. Values are expressed in parts by weight.

TABLE XI

| Example Number | 54 | 55 | 56 | 57 | 58 | 59 | 60 | 61 | 62 |
|---|---|---|---|---|---|---|---|---|---|
| Nucleus | | | | | | | | | |
| Fertiliser compound 10/10/20 aldrin(v) | — | — | — | 84 | 85 | — | — | — | — |
| Potassium nitrate | 8 | 8 | — | — | — | 16 | 16 | 12 | 12 |
| Triammonium phosphate | 13 | 13 | 15 | — | — | 26 | 26 | 25 | 35 |
| Potassium sulphate | 15 | 15 | 18 | — | — | 30 | 30 | 30 | 30 |
| Sodium bithiocarbamate | 50 | 50 | 45 | — | — | — | — | — | — |
| Dimethoate(w) | — | — | — | — | — | 5 | — | 5 | — |
| Vamidothion(x) | — | — | — | — | — | — | 5 | — | 5 |
| Dried clay | 7 | 7 | 5 | — | — | 13 | 13 | 8 | 8 |
| Coating powder | | | | | | | | | |
| Ferric chelate EDDHA(e) | 3 | 3 | 2 | 2 | — | 5 | 5 | — | — |
| 4,6-bis(isopropylamino)-2-methylthio-sym.triazine | 0.2 | — | 0.2 | 0.4 | — | — | — | 0.4 | — |
| 4-ethylamino-6-terbutyl-amino-2-methylthio-sym.triazine | — | 0.2 | — | — | 0.4 | — | — | — | 0.4 |
| Carbon black | 0.2 | 0.2 | 0.1 | 0.1 | — | 0.3 | 0.3 | — | — |
| Potasium nitrate | — | — | 10 | 6.8 | 8.2 | — | — | 12 | 12 |
| Kaolin | 3.3 | 3.3 | 4.3 | 6.3 | 6.1 | 4.4 | 4.4 | 7.2 | 7.2 |
| Coating binder | | | | | | | | | |
| Polyvinyl acetate(r) or Vinyl acetate - chloride | | | | | | | | | |

TABLE XI-continued

| Example Number | 54 | 55 | 56 | 57 | 58 | 59 | 60 | 61 | 62 |
|---|---|---|---|---|---|---|---|---|---|
| copolymer(s) | 0.3 | 0.3 | 0.4 | 0.4 | 0.3 | 0.3 | 0.3 | 0.4 | 0.4 |

(v)Granules of fertiliser as under (u) containing 0.5% of 1,2,3,4-tetrachloro-1,4,4a,5,8,8a-hexahydro 1,4-(dichloromethano)-5,8-methano naphthalene, an active material known under the name of "Aldrin".
(w)O,O-dimethyl S-(N-ethylcarbamoyl)-methyl phosphorodithioate, an active insecticidal material.
(x)O,O-dimethyl-S-2-[1-(N-methylcarbamoyl)ethylthio]ethyl phosphorodithioate, an active insecticidal material.

EXAMPLE 63

Into a drum as described in Example 1 there were charged 690 kg of granules of fertiliser compound having an average diameter of 3mm and an NPK formula of 16/20/0 (d).

The drum is set in rotation and 40 kg of a 5% solution in trichlorethylene of vinyl acetate-chloride copolymer (g) is added. The drum is left turning for 10 minutes and there is then added, at a rate of 10 kg per minute, 198 kg of powder made up as follows:

| | |
|---|---|
| ferrous sulphate | 80 kg |
| ferric chelate ETPA(a) | 40 kg |
| kaolin | 78 kg |

The drum is turned a further 10 minutes and the solvent then evaporated by a strong current of hot air.

There is then added over 20 minutes and simultaneously, 40 kg of 4% ethylcellulose (i) solution in methanol, and 88 kg of powder made up as follows:

| | |
|---|---|
| sodium 2,4-dichloro phenoxyacetate | 64 kg |
| kaolin | 23.9 kg |
| phthalocyanine green PV-01(j) | 0.1 kg. |

The drum is turned for 15 minutes, and the material dried as before.

Green granules corresponding to FIG. 3 are obtained in which the active materials which are incompatible in layers 2 and 2a. These granules constitute a fertiliser for lawns, having an NPK formula of 11.3/13.8/0 and allowing the destruction of weeds occurring in lawns.

EXAMPLES 64 – 73

Working as in Example 63 and using the raw materials below, granules corresponding to FIG. 3 were obtained which were lawn fertilisers permitting the destruction of weeds present in lawns. Values are expressed in parts by weight.

TABLE XII

| Example Number | 64 | 65 | 66 | 67 | 68 | 69 | 70 | 71 | 72 | 73 |
|---|---|---|---|---|---|---|---|---|---|---|
| Nucleus | | | | | | | | | | |
| Fertiliser compound 16/20/20(d) | 81 | 77 | 77 | — | — | — | — | — | — | — |
| Urea beads | — | — | — | 76 | 76 | 75 | 75 | 73 | 72 | 70 |
| First layer (layer 2) | | | | | | | | | | |
| Ferric chelate ETPA(a) | 4 | — | — | 5 | 5 | — | — | 4 | — | 5 |
| Ferric chelate EDDHA(e) | — | 6 | — | — | — | 6 | — | — | 6 | — |
| Ferric chelate EDDHMA(y) | — | — | 6 | — | — | — | 6 | — | — | — |
| Potassium nitrate | — | — | — | — | — | — | — | 6 | 4 | 5 |
| Kaolin or dried clay | 3.9 | 5.85 | 5.85 | 4.9 | 4.9 | 5.85 | 5.85 | 5.8 | 6.8 | 5.8 |
| Binder(f) or (g) | 0.1 | 0.15 | 0.15 | 0.1 | 0.1 | 0.15 | 0.15 | 0.2 | 0.2 | 0.2 |
| Second layer (layer 2a) | | | | | | | | | | |
| Pichloram(t) Potassium salt | 0.1 | 0.1 | 0.1 | 0.04 | 0.04 | — | — | 0.1 | 0.1 | 0.04 |
| Sodium 2,4-dichloro phenoxyacetate | — | — | — | 5 | 5 | 10 | 10 | — | — | 5 |
| Sodium 4-chloro-2-methyl-phenoxyacetate | — | — | — | 5 | — | — | — | — | — | 5 |
| Sodium 2-(4-chloro-2-methyl-phenoxy propionate | — | — | — | — | 5 | — | — | — | — | — |
| Kaolin or dried clay | 2.70 | 2.70 | 2.70 | 3.71 | 3.71 | 2.8 | 2.8 | 2.70 | 2.70 | 3.71 |
| Ethylcellulose(i) | 0.2 | 0.2 | 0.2 | 0.25 | 0.25 | 0.2 | 0.2 | 0.2 | 0.2 | 0.25 |

(y)Ferric chelate of di(sodium-2-hydroxy-5-methyl phenylacetate) ethylene diamine, produced by the applicant under the Trade Mark SEQUESTRENE 157.

EXAMPLES 74 – 80

Operating as stated in Example 1 and using the raw materials noted below, granules corresponding to FIG. 2 are obtained in which the nucleus comprises, as fertiliser, urea covered with a protective layer, and with a coating comprising a selective herbicidal material or an antichlorotic material. Values are expressed in parts by weight.

TABLE XIII

| Example Number | 74 | 75 | 76 | 77 | 78 | 79 | 80 |
|---|---|---|---|---|---|---|---|
| Nucleus and layer 7 | | | | | | | |
| Protected urea beads(z) | 81 | 81 | 93 | 83 | 83 | 87 | 74 |
| Coating powder | | | | | | | |
| Ferric chelate EDDHA(e) | 10 | 5 | 3 | — | — | — | 10 |
| Carbon black | 0.4 | 0.2 | 0.2 | — | — | — | 0.4 |

TABLE XIII-continued

| Example Number | 74 | 75 | 76 | 77 | 78 | 79 | 80 |
|---|---|---|---|---|---|---|---|
| Potassium phospate | — | 7 | — | 10 | 10 | 8 | 7 |
| 4,6-bis(isopropylamino)-2-methylthio sym.triazine | — | — | 0.4 | 0.4 | — | — | — |
| 4-ethylamino-6-terbutylamino 2-methylthio-sym.triazine | — | — | — | — | 0.4 | — | — |
| lichloram(t), potassium salt | — | — | —z | — | — | 0.1 | 0.1 |
| Kaolin | 8.2 | 6.4 | 3.1 | 6.2 | 6.2 | 4.6 | 8 |
| Binder | | | | | | | |
| Polyvinyl acetate(r) or Vinyl acetate-chloride copolymer(s) | 0.4 | 0.4 | 0.3 | 0.4 | 0.4 | 0.3 | 0.5 |

(z)Urea beads coated with a layer of urea-formaldehyde resin by addition of formaldehyde on the surface of the beads.

Similar products to those described in Examples 74 to 80 are obtained by using, in these examples, in place of the binders indicated, the same quantities of other polymers in solution, such as those cited in Table I.

EXAMPLES 81 – 100

Operating as described in Experiment E and using the raw materials noted below in Table XIII and in Table XIV, granules corresponding to FIG. 3 were obtained. The nuclei of these granules comprise sodium chlorate and optionally an incombustible substance which can be dried clay or sodium borate, the intermediary coating being of incombustible material and the outer coating comprising organic herbicides and incombustible fillers. Values are expressed in parts by weight.

TABLE XIV

| | 81 | 82 | 83 | 84 | 85 | 86 | 87 | 88 | 89 | 90 |
|---|---|---|---|---|---|---|---|---|---|---|
| Nucleus | | | | | | | | | | |
| Sodium tetraborate | — | — | — | — | 20 | — | — | 30 | 30 | — |
| Sodium chlorate | 73 | 66 | 65 | 69 | 40 | 70 | 65 | 40 | 40 | 72 |
| Dried clay | — | 9 | — | — | 10 | — | — | — | — | — |
| Intermediary coating | | | | | | | | | | |
| Kaolin or dried clay | 4 | 7,5 | 5 | 2 | — | 3 | 7 | 2,9 | 4,9 | 2 |
| Antimony oxide | — | — | — | 2 | — | — | — | — | — | 2 |
| Powdered cryolite | 2 | — | — | — | ·5 | 2 | — | — | — | — |
| Boric acid | — | — | 6,8 | — | — | 4,9 | — | — | — | — |
| Sodium chlorate | 3,9 | 7,5 | — | — | — | — | 7,8 | — | — | — |
| Sodium fluoroborate | — | — | — | 3,8 | — | — | — | 7 | — | 3,8 |
| Sodium silicate(a₁) | — | — | — | — | 4,8 | — | — | — | 5 | — |
| Binder(f₁) | 0,1 | 0,1 | 0,1 | 0,3 | 0,2 | 0,1 | 0,2 | 0,1 | 0,1 | 0,2 |
| Outer coating | | | | | | | | | | |
| 3-Amino-1,2,4-triazole, | 2 | — | — | 2 | — | 2 | — | 2 | — | 2 |
| Pichloram(g₁), potassium salt | — | — | 0,1 | — | — | — | 0,1 | — | — | — |
| 2-Chloro-4-ethylamino-6-tert.butylamino-s-triazine | 1,6 | 4 | 4 | — | — | 2 | 2 | 2 | 2 | |
| 4-Ethylamino-6-sec.butylamino-2-methoxy-s-triazine | 1,6 | — | — | 4 | 4 | 2 | 2 | 1 | 1 | |
| 6-sec.Butylamino-2-methoxy-4-methylamino-s-triazine | — | — | — | — | — | — | — | 1 | 1 | — |
| Methylthiotriazine(e₁) | — | — | 2 | 2 | — | — | — | — | — | — |
| Sodium chloride | 6 | 2,5 | 7 | 5 | 10 | 4 | 10 | 6 | 10 | 6 |
| Sodium fluoroborate | 2 | — | 3 | 3 | — | 4 | — | 2 | — | 2 |
| Kaolin or dried clay | 4,6 | 4,05 | 6,4 | 6,0 | 5,5 | 5,5 | 5,4 | 5,5 | 5,5 | 5,5 |
| Violet pigment | — | 0,01 | — | 0,02 | — | — | — | — | 0,02 | — |
| Binder(f₁) | 0,4 | 0,14 | 0,6 | 0,88 | 0,5 | 0,5 | 0,5 | 0,5 | 0,48 | 0,5 |

(e₁)one of the following compounds or a mixture comprising two or more of the following compounds:
4,6-bis-(isopropylamino)-2-methylthio-s-triazine
6-isopropylamino-4-methylamino-2-methyl-thio-s-triazine
4,6-bis-(ethylamino)-6-isopropylamino-2-methyl-thio-s-triazine
4-ethylamino-6-isopropylamino-6-isopropylamino-2-methyl-thio-s-triazine
4-ethylamino-6-secbutylamino-2-methylthio-s-triazine butylamino-2-methylthio-s-triazine
(f₁)A 7% by weight-solution of the polyvinyl acetate defined under d₁ in methylene chloride is used or a 7% -solution of vinyl chloride (85%) and vinyl acetate (15%) copolymer in tetrachloroethylene.
(g₁)current name of 4-amino-3,5-trichloro-picolonic acid the potassium salt of which is used.

TABLE XV

| | 91 | 92 | 93 | 94 | 95 | 96 | 97 | 98 | 99 | 100 |
|---|---|---|---|---|---|---|---|---|---|---|
| Nucleus | | | | | | | | | | |
| Sodium chlorate | 56 | 65 | 65 | 41 | 35 | 42,5 | 45 | 60 | 63 | 23 |
| Sodium chloride | 15 | — | — | — | — | 25,5 | — | — | — | 69 |
| Sodium tetraborate | — | — | — | 41 | 35 | — | — | — | — | — |
| Sodium silicate | — | — | 13 | — | — | — | — | 12 | — | — |
| Dried clay | — | — | — | — | 3 | 17,0 | 45 | 6 | 7 | — |
| Intermediary coating | | | | | | | | | | |
| Powdered brick | — | 4,8 | — | — | — | 2 | — | 4 | 7,8 | — |
| Kaolin | 10 | — | 3,9 | 3 | 3,85 | 2,9 | 3 | 3,85 | — | 2 |
| Magnesia | — | 3 | — | — | 1 | — | — | — | 2 | — |

TABLE XV-continued

|  | 91 | 92 | 93 | 94 | 95 | 96 | 97 | 98 | 99 | 100 |
|---|---|---|---|---|---|---|---|---|---|---|
| Borax($a_1$) | 5 | 2 | — | 4,9 | 2 | — | — | — | 7 | — |
| Boric acid | — | 2 | 4 | — | 10 | 3 | — | — | 3 | — |
| Trisodium phos.($a_1$) | 3 | — | — | — | — | 2 | — | 5 | — | — |
| Sodium chloride | — | 8 | 4 | — | — | — | 3,9 | 3 | — | 0,95 |
| Binder($f_1$) | 0,2 | 0,2 | 0,1 | 0,1 | 0,15 | 0,1 | 0,1 | 0,15 | 0,2 | 0,05 |
| Coating | | | | | | | | | | |
| Bromacil($h_1$) | | | | | | | | | | |
| Isocil($h_1'$) | 3 | 3 | 2 | — | — | — | — | — | — | — |
| "Benzomarc"($i_1$) | — | — | — | 2 | — | — | — | — | — | — |
| 17623-RP($j_1$) | — | — | — | — | 3 | — | — | — | — | — |
| Fenac($k_1$) or TBA($m_1$) | — | 0,75 | — | — | — | 2 | — | — | — | — |
| Dicamba($l_1$) | — | — | — | — | — | — | 0,5 | — | — | — |
| TFP($n_1$) | — | — | — | — | — | — | — | 3 | — | — |
| Dichlobenil($o_1$) or Chlorothiamide($p_1$) | — | — | — | — | — | — | — | — | 4 | — |
| Flurenol($q_1$) | — | — | 0,2 | — | — | — | 0,5 | — | — | 0,5 |
| Kaolin | 3 | — | 2 | 2 | 1,3 | — | 0,6 | 2 | — | 2 |
| Powdered brick | — | 4 | — | 2 | — | 1,9 | 0,6 | — | 2,5 | — |
| Titanium oxide | 1 | — | — | — | — | — | — | — | 0,5 | — |
| Iron oxide, $Fe_2O_3$ | — | 1 | — | — | 0,5 | — | — | — | — | — |
| Carbon black | — | — | — | 1 | — | — | 0,2 | — | — | — |
| Blue pigment | 0,3 | — | 0,3 | — | — | — | 0,1 | — | — | — |
| Sodium chloride | — | 2 | 4 | — | 4 | 1 | — | — | 2,8 | — |
| Potassium cyanate | — | 3 | — | — | — | — | — | — | — | 2 |
| Sodium fluoroborate | — | 1 | — | — | 1 | — | — | — | — | — |
| Borax | 2,5 | — | — | 2,7 | — | — | 1 | — | — | — |
| Boric acid | 1 | — | 1 | — | — | — | — | 0,9 | — | — |
| Binder($f_1$) | 0,2 | 0,25 | — | — | 0,2 | 0,1 | — | 0,1 | 0,2 | — |
| Polystyrene($r_1$) | — | — | — | 0,3 | — | — | — | — | — | 0,5 |
| Ethylcellulose($s_1$) | — | — | 0,4 | — | — | — | 0,1 | — | — | — |
| Diethylphthalate | — | — | 0,1 | — | — | — | — | — | — | — |

($h_1$)common name of 5-bromo-6-methyl-3-sec.butyl-uracil
($h_1'$)common name of 5-bromo-6-methyl-3-isopropyluracil
($i_1$)name used to designate N-benzoyl-N-(3,4-dichloro-phenyl)-N',N'-dimethylurea
($j_1$)name used to designate 4-(2,4-dichloro-5-isopropoxy-phenyl)-5-oxo-2-tert.-butyl-1,3,4-oxadiazoline
($k_1$)common name of 2,3,6-trichloro-phenylacetic acid
($l_1$)common name of 3,6-dichloro-2-methoxy-benzoic acid
($m_1$)common name of 2,4,6-trichloro-benzoic acid
($n_1$)common name of sodium 2,2,3,3-tetrafluoropropionate
($o_1$)common name of 2,6-dichloro benzonitrile
($p_1$)common name of 2,6-dichloro thiobenzamide
($q_1$)common name of 9-hydroxy-9-butoxycarbonylfluorene
($r_1$)non-modified polystyrene used as a 3% by weight-solution in methylene chloride
($s_1$)compound possessing an ethoxy-ratio comprised between 48,5 and 49% by weight and used as a 4% by weight-solution in methylene chloride. When ethyl phtalate is to be used as a plasticizer, it is added to the solution.

What is claimed is:

1. Coated granular product for the treatment of soil which comprises a central solid nucleus, constituting from about 65 to 99% of the weight of the granule, said nucleus consisting of at least 40 to 100% of its weight of a fertilizer material which is soluble in water without decomposition, and a coating of one or several layers constituting from about 1 to 35% of the weight of the granule, at least one layer of said coating comprising particles of an active substance different from that of the nucleus and selected from fertilizers and substances providing plants with oligo-elements, said granular product being characterized in that said layers essentially consist of a. from about 90 to 99%, calculated on the weight of said coating, of particles of a solid material having an average main diameter not exceeding 0.2mm of which at least 25%, calculated on the weight of the coating, consist of a material soluble in water without decomposition in the ratio of at least 1 gram of substance for 50 grams of water and b. from about 1 to 10%, calculated on the weight of said coating, of a water-insoluble, solid, plastified or nonplastified, non-cured resin, said granular product being non-dusty and non-hygroscopic but releasing the active materials of the coating and of the nucleus, without any delay as soon as said product is brought into contact with the moisture of the soil.

2. A coated grannular product as defined in claim 1, wherein the solubility of the said soluble fertilizer of the central nucleus is at least 1 gram per 100 grams water (20° C).

3. A coated grannular product as defined in claim 1, wherein the solubility of the said soluble fertilizer of the central nucleus is at least 10 gram per 100 grams water (20° C).

4. A coated grannular product as defined in claim 1, wherein the coating consists of at least two layers of different composition, comprising at least an intermediary coating and an outer coating.

5. A coated grannular product as defined in claim 1, wherein the average value of the major diameter of the nucleus is between 0.6 and 16 mm.

6. A coated grannular product as defined in claim 1, wherein the average value of the major diameter of the granule is between 0.6 and 20 mm.

7. A coated grannular product as defined in claim 1, wherein the average value of the major diameter of the said particles of solid material is between 0.001 and about 0.1 mm.

8. A coated grannular product as defined in claim 7, wherein the portion of particles of solid material of the coating which consists of material soluble in water without decomposition constitutes from half to two-thirds of the solid particles.

9. A coated grannular product as defined in claim 8, wherein between 15 and 85% of the weight of solid particles of the coating consists of particles of active substance and the remainder of inert material.

10. A coated grannular product as defined in claim 9, wherein the solid particles of the coating comprise particles of material providing oligo-elements to plants with or without particles of inert material.

11. Product as defined in claim 9, wherein the solid particles of the coating comprise particles of fertiliser.

12. A coated grannular product as defined in claim 1, wherein the total weight of the coating of the granules is between about 10 and 35% of the total weight of the granular product.

13. A coated grannular product as defined in claim 1, wherein said coating comprised an intermediary coating and an outer coating, said intermediary coating containing at least one solid incombustible material and a resin binding said material to the nucleus, said intermediary and outer coatings, each consisting in a proportion of at least 40% by weight, of said water soluble particles.

14. A coated grannular product as defined in claim 1, wherein said solid polymeric resin consists essentially of polyvinyl acetate.

15. A coated grannular product as defined in claim 1, wherein said solid polymeric resin consists essentially of a copolymer of vinyl chloride and vinyl acetate.

16. A coated granular product according to claim 1, wherein the active substance present in at least one layer of the coating is a fertilizer.

17. A coated granular product as defined in claim 16, wherein the particles of a solid material recited in (a) consist of at least 40%, calculated on the weight of the coating, of a material soluble in water without decomposition in the ratio of at least 1 gram of substance per 50 grams of water.

18. A coated granular product according to claim 1, wherein the nucleus consists essentially of potassium nitrate, ammonium phosphate, ammonium sulphate, dicalcium phosphate, potassium nitrate and potassium sulphate and wherein the coating consists essentially of particles of magnesium sulphate, a ferric chelate of sodium diethylenetriaminopentacetate, kaolin, manganese sulphate, nickel sulphate, zinc sulphate, copper sulphate, sodium borate and a pigment and a high molecular weight polyvinyl acetate resin.

19. A coated granular product as defined in claim 1, wherein the total weight of the coating of the granules is between 10 and 35% of the total weight of the granular product and the particles of a solid material recited in (a) consist of at least 40%, calculated on the weight of the coating, of a material soluble in water without decomposition in the ratio of at least 1 gram of substance per 50 grams of water.

* * * * *